United States Patent
Okamoto et al.

(10) Patent No.: US 10,733,735 B2
(45) Date of Patent: Aug. 4, 2020

(54) OPHTHALMIC APPARATUS

(71) Applicant: Tomey Corporation, Nagoya-shi (JP)

(72) Inventors: Keiichiro Okamoto, Nagoya (JP); Fushi Li, Nagoya (JP); Kenji Horikoshi, Nagoya (JP)

(73) Assignee: TOMEY CORPORATION, Nagoya-Shi (JP)

( * ) Notice: Subject to any disclaimer, the term of this patent is extended or adjusted under 35 U.S.C. 154(b) by 353 days.

(21) Appl. No.: 15/843,059

(22) Filed: Dec. 15, 2017

(65) Prior Publication Data

US 2018/0174296 A1    Jun. 21, 2018

(30) Foreign Application Priority Data

Dec. 16, 2016 (JP) ................. 2016-244768

(51) Int. Cl.
| | |
|---|---|
| G06T 7/00 | (2017.01) |
| A61B 3/10 | (2006.01) |
| A61B 3/117 | (2006.01) |
| A61B 3/00 | (2006.01) |
| A61B 3/107 | (2006.01) |
| G06T 7/60 | (2017.01) |

(52) U.S. Cl.
CPC .......... G06T 7/0016 (2013.01); A61B 3/0025 (2013.01); A61B 3/0058 (2013.01);
(Continued)

(58) Field of Classification Search
CPC .............. G06T 7/0016; G06T 7/60; G06T 2207/30041; G06T 2207/10072;
(Continued)

(56) References Cited

U.S. PATENT DOCUMENTS

| | | |
|---|---|---|
| 6,626,538 B1 | 9/2003 | Arrowsmith |
| 2003/0133074 A1 | 7/2003 | Petit et al. |
| | (Continued) | |

FOREIGN PATENT DOCUMENTS

| | | | | |
|---|---|---|---|---|
| EP | 2583619 A1 * | 4/2013 | ............ | A61B 3/107 |
| EP | 2583619 A1 | 4/2013 | | |
| | (Continued) | | | |

*Primary Examiner* — William R Alexander
*Assistant Examiner* — Henry A Duong
(74) *Attorney, Agent, or Firm* — Shumaker, Loop & Kendrick, LLP

(57) ABSTRACT

An ophthalmic apparatus that may include a processor; and a memory storing computer-readable instructions therein, the computer-readable instructions, when executed by the processor, causing the ophthalmic apparatus to perform: acquiring a two-dimensional tomographic image of the subjected eye; calculating a preoperative shape of the subjected eye based on a preoperative two-dimensional tomographic image of a preoperative subjected eye acquired by the acquiring of the two-dimensional tomographic image; calculating a postoperative shape of the subjected eye based on a postoperative two-dimensional tomographic image of a postoperative subjected eye acquired by the acquiring of the two-dimensional tomographic image; and calculating a displacement amount between a first reference axis obtained from the preoperative two-dimensional tomographic image of the preoperative subjected eye and a second reference axis obtained from the postoperative two-dimensional tomographic image of the postoperative subjected eye, based on the calculated preoperative shape and the calculated postoperative shape.

19 Claims, 11 Drawing Sheets

(52) U.S. Cl.
CPC .............. *A61B 3/102* (2013.01); *A61B 3/107* (2013.01); *A61B 3/117* (2013.01); *G06T 7/60* (2013.01); *G06T 2207/10072* (2013.01); *G06T 2207/30041* (2013.01)

(58) Field of Classification Search
CPC ..... A61B 3/0058; A61B 3/107; A61B 3/0025; A61B 3/117; A61B 3/102; A61B 3/1025; A61B 3/12; A61B 3/1233; A61B 3/1241; A61B 3/14; A61B 3/145
USPC .......................................................... 351/206
See application file for complete search history.

(56) References Cited

U.S. PATENT DOCUMENTS

| | | |
|---|---|---|
| 2003/0133075 A1 | 7/2003 | Sheets, Jr. et al. |
| 2012/0197102 A1 | 8/2012 | Hanebuchi et al. |
| 2013/0107208 A1 | 5/2013 | Endo |
| 2017/0273558 A1 | 9/2017 | Tamura |

FOREIGN PATENT DOCUMENTS

| | | | | |
|---|---|---|---|---|
| EP | 2594192 | A1 | 5/2013 | |
| EP | 2865324 | A1 * | 4/2015 | ............. A61B 3/102 |
| EP | 2865324 | A1 | 4/2015 | |
| JP | 2572979 | B2 | 1/1997 | |
| JP | 2003245301 | A | 9/2003 | |
| JP | 2010220757 | A | 10/2010 | |
| JP | 2012152469 | A | 8/2012 | |
| JP | 2014533150 | A | 12/2014 | |
| JP | 2016-029968 | A | 3/2016 | |
| JP | 5887839 | B2 | 3/2016 | |
| JP | 2016-054854 | A | 4/2016 | |
| WO | 2013057307 | A1 | 4/2013 | |

* cited by examiner

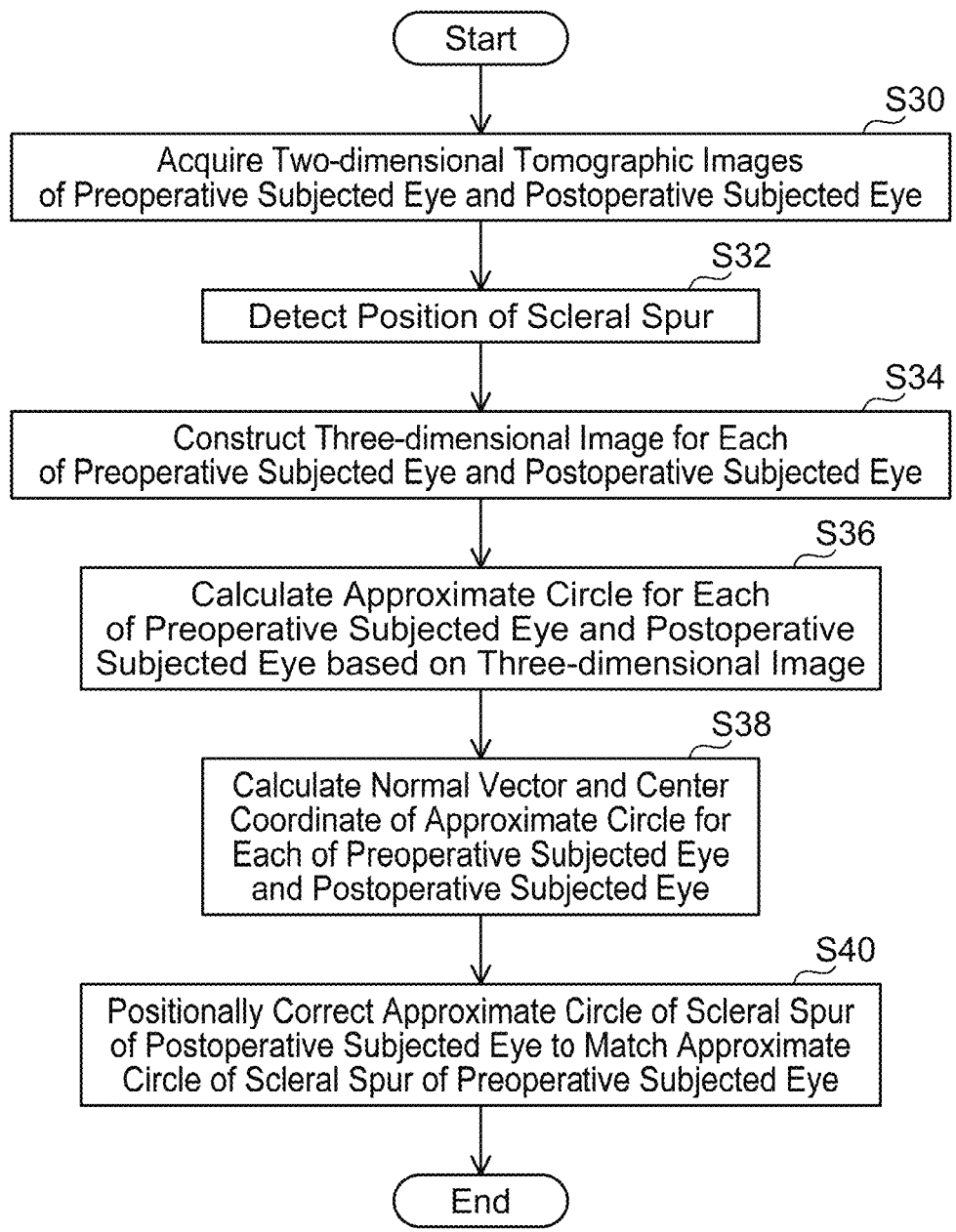

OPHTHALMIC APPARATUS

TECHNICAL FIELD

The technique disclosed herein relates to an ophthalmic apparatus configured to measure a shape of a subjected eye. More specifically, it relates to an ophthalmic apparatus capable of evaluating preoperative and postoperative shapes of the subjected eye.

BACKGROUND ART

An ophthalmic apparatus for measuring a shape of a targeted portion of a subjected eye (such as a cornea, an anterior chamber, a crystalline lens, and the like) is being developed. For example, an ophthalmic apparatus described in Japanese Patent Application Publication No. 2016-054854 includes a measurement optical system that irradiates light from a light source into a subjected eye and guides reflected light thereof, and a reference optical system that irradiates the light from the light source to a reference surface and guides reflected light thereof. When measurement is to be performed, a position of a targeted portion in the subjected eye is identified using interference light, which multiplexed the reflected light guided in the measurement optical system and the reflected light guided in the reference optical system. Further, a shape of the targeted portion is calculated from the identified position of the targeted portion. The ophthalmic apparatus further includes a vision-fixation lamp, and a visual axis of the subjected eye is fixed by prompting the subjected eye to stare at the vision-fixation lamp during the measurement.

SUMMARY

In a case of performing a cataract surgery, a preoperative eye shape measurement is performed to determine contents of the surgery. On the other hand, after the cataract surgery has been performed, the eye shape may have changed due to an influence of the surgery. Due to this, a postoperative eye shape measurement needs to be performed to evaluate the change between the eye shapes before and after the surgery. To accurately compare the preoperative shape and the postoperative shape of a subjected eye, a visual axis of the subjected eye at a time of the preoperative measurement and a visual axis of the subjected eye at a time of the postoperative measurement need to match to each other. In the ophthalmic apparatus of Japanese Patent Application Publication No. 2016-054854, the visual axis of the subjected eye during the measurements is fixed by prompting the subjected eye to stare at the vision-fixation lamp. However, the preoperative subjected eye may have deteriorated vision, and in such a case, staring at the vision-fixation lamp becomes difficult. Due to this, the visual axis of the subjected eye at the time of the preoperative measurement and the visual axis of the subjected eye at the time of the postoperative measurement do not match to each other, and there was a problem that the preoperative eye shape and the postoperative eye shape could not be compared accurately. The disclosure herein provides a technique that accurately evaluates a change between a preoperative shape and a postoperative shape of a subjected eye.

An ophthalmic apparatus disclosed herein may be configured to measure a shape of a subjected eye, the apparatus comprising: a processor; and a memory storing computer-readable instructions therein, the computer-readable instructions, when executed by the processor, causing the ophthalmic apparatus to perform: acquiring a two-dimensional tomographic image of the subjected eye; calculating a preoperative shape of the subjected eye based on a preoperative two-dimensional tomographic image of a preoperative subjected eye acquired by the acquiring of the two-dimensional tomographic image; calculating a postoperative shape of the subjected eye based on a postoperative two-dimensional tomographic image of a postoperative subjected eye acquired by the acquiring of the two-dimensional tomographic image; and calculating a displacement amount between a first reference axis obtained from the preoperative two-dimensional tomographic image of the preoperative subjected eye and a second reference axis obtained from the postoperative two-dimensional tomographic image of the postoperative subjected eye, based on the calculated preoperative shape and the calculated postoperative shape.

BRIEF DESCRIPTION OF DRAWINGS

FIG. 5 is a flow chart showing an example of a procedure for correcting a displacement amount based on a scleral spur using the ophthalmic apparatus of the first embodiment;

DETAILED DESCRIPTION

Figure 1:
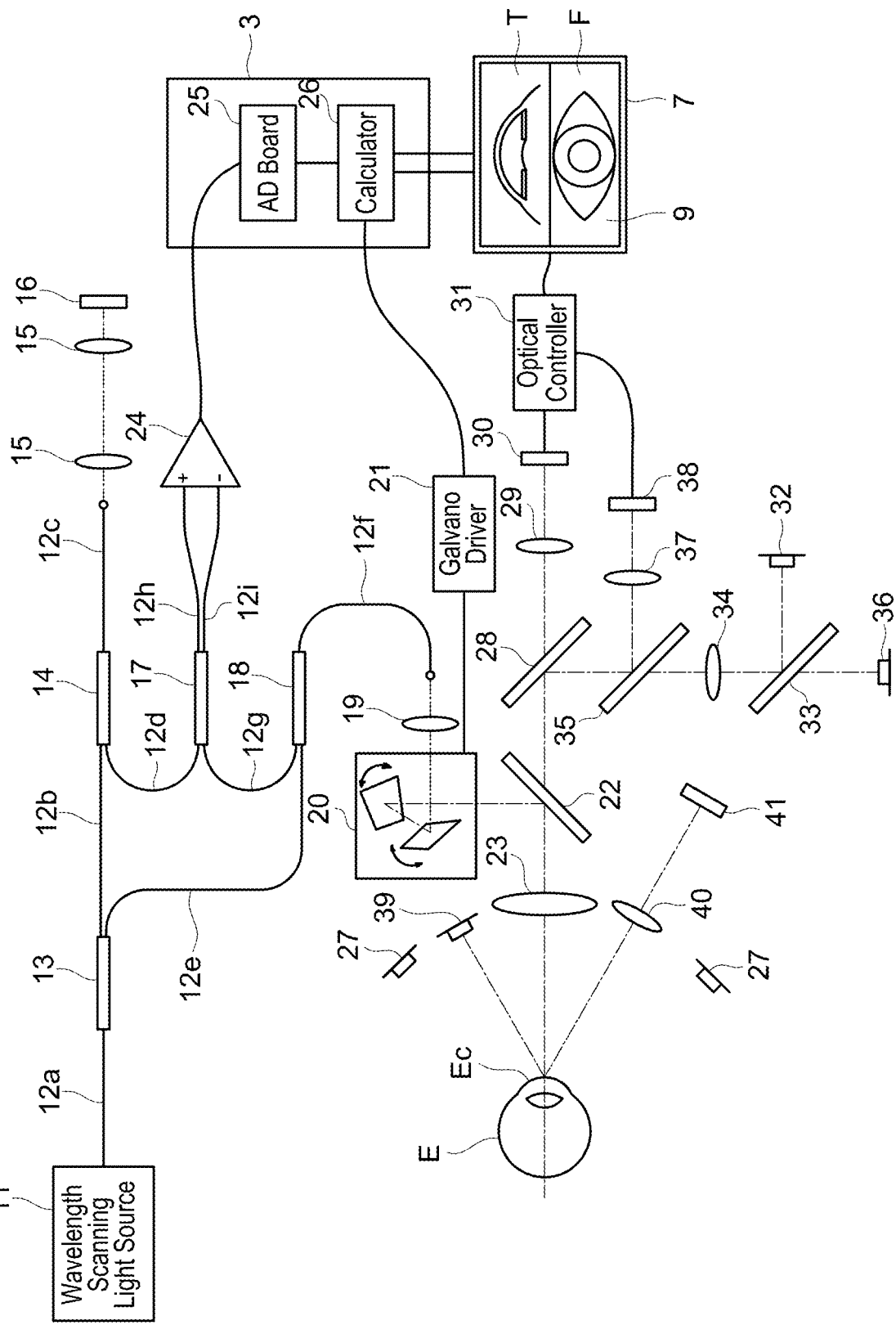
FIG. 1 is a schematic configuration of an optical system of an ophthalmic apparatus of a first embodiment.

Some of the features characteristic to below-described embodiments will herein be listed. It should be noted that the respective technical elements are independent of one another, and are useful solely or in combinations. The combinations thereof are not limited to those described in the claims as originally filed.

An ophthalmic apparatus disclosed herein may be configured to measure a shape of a subjected eye, the apparatus comprising: a processor; and a memory storing computer-readable instructions therein, the computer-readable instructions, when executed by the processor, causing the ophthalmic apparatus to perform: acquiring a two-dimensional tomographic image of the subjected eye; calculating a preoperative shape of the subjected eye based on a preoperative two-dimensional tomographic image of a preoperative subjected eye acquired by the acquiring of the two-dimensional tomographic image; calculating a postoperative shape of the subjected eye based on a postoperative two-dimensional tomographic image of a postoperative subjected eye acquired by the acquiring of the two-dimensional tomographic image; and calculating a displacement amount between a first reference axis obtained from the preoperative two-dimensional tomographic image of the preoperative subjected eye and a second reference axis obtained from the postoperative two-dimensional tomographic image of the postoperative subjected eye, based on the calculated preoperative shape and the calculated postoperative shape.

In the ophthalmic apparatus as above, in the two-dimensional tomographic image of the preoperative subjected eye and the two-dimensional tomographic image of the postoperative subjected eye, the displacement amount between the first reference axis acquired from the two-dimensional tomographic image of the preoperative subjected eye and the second reference axis acquired from the two-dimensional tomographic image of the postoperative subjected eye is calculated. Due to this, even if a state of the preoperative subjected eye and a state of the postoperative subjected eye are different, the first reference axis of the preoperative subjected eye and the second reference axis of the postoperative subjected eye can be corrected based on the displacement amount calculated from the first reference axis acquired from the two-dimensional tomographic image of the preoperative subjected eye and the second reference axis acquired from the two-dimensional tomographic image of the postoperative subjected eye. Due to this, the preoperative shape and the postoperative shape of the subjected eye can suitably be compared.

In the ophthalmic apparatus disclosed herein, each of the first and second reference axes may be calculated from an internal shape of the subjected eye according to a preset procedure. The internal shape of the subjected eye may include at least one of a shape of an angle of an anterior chamber, a corneal shape, a corneal limbus shape, and a pupil shape. According to this configuration, each of the first and second reference axes is calculated based on at least one of the shape of the angle of the anterior chamber, the corneal shape, the corneal limbus shape, and the pupil shape. Due to this, each of the first and second reference axes can be calculated by setting a portion where shape change is less likely to occur before and after a surgery (that is, the angle of anterior chamber, the cornea, the corneal limbus, and/or the pupil) as a reference. Thus, a displacement amount between the first reference axis of the preoperative subjected eye and the second reference axis of the postoperative subjected eye can be calculated accurately.

In the ophthalmic apparatus disclosed herein, the computer-readable instructions further may cause the ophthalmic apparatus to perform correcting at least one of the preoperative two-dimensional tomographic image and the postoperative two-dimensional tomographic image based on the calculated displacement amount to match the first reference axis of the preoperative subjected eye and the second reference axis of the postoperative subjected eye to each other. According to this configuration, in the two-dimensional tomographic image(s) that had the displacement amount corrected, the first reference axis of the subjected eye thereof matches the second reference axis of the subjected eye in the corresponding two-dimensional tomographic image, and thus the preoperative shape and the postoperative shape of the subjected eye can suitably be compared.

In the ophthalmic apparatus disclosed herein, the computer-readable instructions further may cause the ophthalmic apparatus to perform calculating a positional displacement amount at a preset portion of the subjected eye before and after a surgery by comparing the preoperative two-dimensional tomographic image and the postoperative two-dimensional tomographic image, one of or both of which have been corrected in the correcting of at least one of the two-dimensional tomographic images. The memory may be further configured to store information related to the positional displacement amount calculated in the calculating of the positional displacement amount. The computer-readable instructions further may cause the ophthalmic apparatus to perform predicting a shape of the postoperative subjected eye based on the preoperative two-dimensional tomographic image of the preoperative subjected eye acquired by the acquiring of the two-dimensional tomographic image and the information related to the positional displacement amount stored in the memory. According to this configuration, the preoperative subjected eye and the postoperative subjected eye can be compared in a state where a displacement in the first and second reference axes has been corrected, so a change (positional displacement amount) in the shape of each portion of the subjected eye can accurately be calculated. Further, since the shape change in the postoperative subjected eye is predicted based on the accurately-calculated positional displacement amount, a prediction accuracy of the change in the postoperative shape of the subjected eye can be improved.

In the ophthalmic apparatus disclosed herein, the computer-readable instructions further may cause the ophthalmic apparatus to perform displaying information related to the preoperative shape of the subjected eye, information related to the postoperative shape of the subjected eye, and the information related to the displacement amount. According to this configuration, the preoperative shape, the postoperative shape, and the displacement amount of the subjected eye are displayed by this display, so the change between the preoperative shape of the subjected eye and the postoperative shape thereof can be recognized.

In the ophthalmic apparatus disclosed herein, the information related to the preoperative shape of the subjected eye may be the preoperative two-dimensional tomographic image of the preoperative subjected eye, and the information related to the postoperative shape of the subjected eye may be the postoperative two-dimensional tomographic image of the postoperative subjected eye. The at least one of the preoperative two-dimensional tomographic image of the preoperative subjected eye and the postoperative two-dimensional tomographic image of the postoperative subjected eye may be corrected in the correcting of at least one of the two-dimensional tomographic images. The displaying may be performed to display at least one of an image that displays the preoperative two-dimensional tomographic image of the preoperative subjected eye adjacent to the postoperative two-dimensional tomographic image of the postoperative subjected eye, and an image that displays one of the preoperative two-dimensional tomographic image of the preoperative subjected eye and the postoperative two-dimensional tomographic image of the postoperative subjected eye being superimposed over the other thereof. According to this configuration, the preoperative shape and the postoperative shape of the subjected eye, with the displacement between their first and second reference axes having been corrected, can be displayed adjacent to each other and/or by superimposing them on top of each other, and thus the change between the preoperative shape of the subjected eye and the postoperative shape thereof can be recognized easily.

In the ophthalmic apparatus disclosed herein, each of the information related to the preoperative shape of the subjected eye and the information related to the postoperative shape of the subjected eye to be displayed by the displaying may include at least one of a corneal shape, shapes of a crystalline lens and an intraocular lens, intraocular positions of the crystalline lens and the intraocular lens, and a shape of an angle of an anterior chamber. According to this configuration, changes of shapes of the cornea, the crystalline lens and the intraocular lens, and the angle of the anterior chamber, which greatly influence postoperative visual function, and the intraocular positions of the crystalline lens and the intraocular lens can be recognized.

In the ophthalmic apparatus disclosed herein, the computer-readable instructions further may cause the ophthalmic apparatus to perform: acquiring a corneal shape map of the subjected eye; and correcting at least one of a corneal shape map of the preoperative subjected eye and a corneal shape map of the postoperative subjected eye that are acquired by the acquiring of the corneal shape map, based on the calculated displacement amount, to match the first reference axis of the preoperative subjected eye and the second reference axis of the postoperative subjected eye to each other. According to this configuration, in the corneal shape map(s) with the displacement amount having been corrected, the first and second reference axes of the subjected eye match to each other, so the preoperative shape and the postoperative shape of the subjected eye can suitably be compared.

In the ophthalmic apparatus disclosed herein, the computer-readable instructions further may cause the ophthalmic apparatus to perform displaying at least one of an image that displays the corneal shape map of the preoperative subjected eye and the corneal shape map of the postoperative subjected eye, one of or both of which have been corrected by the correcting of the at least one of the corneal shape maps, and an image that displays a differential map of the corneal shape map of the preoperative subjected eye and the corneal shape map of the postoperative subjected eye. According to this configuration, the change between the preoperative shape of the subjected eye and the postoperative shape thereof can easily be recognized.

First Embodiment

Hereinbelow, an embodiment according to the present disclosure will be described with reference to the drawings. FIG. 1 shows an optical system for capturing tomographic images of an anterior eye Ec of a subjected eye E using an anterior eye optical coherence tomographic image capturing apparatus 1. The anterior eye optical coherence tomographic image capturing apparatus 1 (hereinbelow referred to as "anterior eye OCT apparatus 1") is an apparatus used for an ophthalmological examination of the anterior eye Ec of an eyeball of a subject (subjected eye E) (see FIG. 1), such as measurements of an angle of the eye, curvature of a cornea, corneal thickness distribution, anterior chamber depth, and the like, and for an ophthalmological diagnosis that is to display tomographic images of the anterior eye Ec including an area thereof from a cornea 122 to an iris 128 (see FIG. 6) and a crystalline lens on a monitor. The anterior eye OCT apparatus 1 captures tomographic images of the anterior eye Ec of the subjected eye E by an optical coherence tomography (OCT). In this embodiment, the anterior eye OCT apparatus 1, which is one type of an anterior eye tomographic image capturing apparatus, is used, however, no limitation is made to this configuration. Other than the anterior eye OCT apparatus 1, an ultrasound imaging and diagnostic apparatus and the like using ultrasound may be used, for example, and any device capable of capturing tomographic images of the anterior eye Ec can be employed.

Although not shown, a main body of the anterior eye OCT apparatus 1 is supported so as to be movable in an X direction (left-and-right direction), in a Y direction (up-and-down direction), and in a Z direction (front-and-rear direction) relative to a holding table. A chin support and a forehead pad are fixed relative to the holding table on a front face side (subject side) of the main body. When the subject puts the chin on the chin support and puts the forehead against the forehead pad, the subject's eye (subjected eye E) comes to be positioned in front of an inspection window for capturing images (through which light comes in and goes out) which is provided in a front face of the main body.

Figure 2:
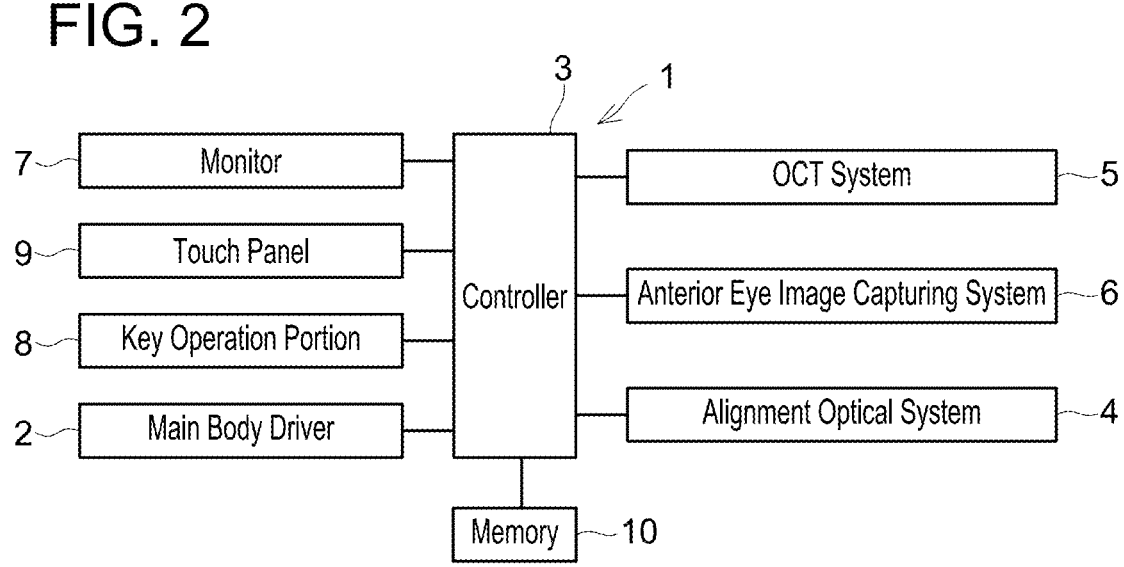
FIG. 2 is a block diagram of a control system of the ophthalmic apparatus of the first embodiment.

As shown in FIG. 2, the anterior eye OCT apparatus 1 includes a main body driver 2 configured to move the main body relative to the holding table freely in each of the X, Y, and Z directions. The main body driver 2, although details thereof are omitted, includes a well-known configuration including an X-direction movement motor, a Y-direction movement motor, a Z-direction movement motor, and the like, and is controlled by a controller 3. As described later, the main body driver 2 and the controller 3, together with an alignment optical system 4, constitute an alignment unit and an auto eye tracking unit.

As shown in FIG. 2, the main body includes the controller 3, the alignment optical system 4, an OCT system 5, and an anterior eye image capturing system 6. The controller 3 includes a microcomputer including a CPU, a memory, and the like and is configured to perform overall control of the anterior eye OCT apparatus 1. The OCT system 5 acquires a three-dimensional tomographic image of the anterior eye Ec (hereinbelow referred to as "anterior eye 3D image") constituted of a plurality of two-dimensional tomographic images. The anterior eye image capturing system 6 captures a front image of the subjected eye E. As aforementioned, the alignment optical system 4 constitutes the alignment unit and the auto eye tracking unit, as well as a corneal apex position detecting unit. Details of the OCT system 5, the anterior eye image capturing system 6, and the alignment optical system 4 will be described later.

Further, the main body includes a monitor 7 and an operation portion 8. The monitor 7 is positioned on a rear face side (examiner's side) and is configured to display a front image F (see FIG. 1) of the subjected eye E. The operation portion 8 is an interface for the examiner to perform various kinds of operations. Although not shown, the operation portion 8 includes a measurement start switch, a measurement region designating switch, a keyboard, a mouse, and the like. Further, in FIG. 2, a touch panel 9 is shown as a separate element from the operation portion 8, however, the touch panel 9 may be included in the operation portion 8. The touch panel 9 is arranged integrally with a screen of the monitor 7.

The controller 3 is connected to a memory 10. The memory 10 is a device capable of storing data on a computer-readable recording medium, such as a hard disk, a CD-ROM/RAM, a DVD-ROM/RAM, and a semiconductor memory. The memory 10 stores image data of the captured anterior eye 3D image, and the like.

The OCT system 5 is a system configured to acquire tomographic images (cross sectional images) of the anterior eye Ec by the OCT. In the present embodiment, a Fourier domain (optical frequency sweep) system is employed in which a wavelength scanning light source 11 which performs scans while temporally changing a wavelength is used.

As shown in FIG. 1, light outputted from the wavelength scanning light source 11 is inputted to a first fiber coupler 13 through an optical fiber 12a. The light inputted to the first fiber coupler 13 is demultiplexed into reference light and measurement light, for example at a ratio of 1:99, in the first fiber coupler 13, and each light is outputted. The reference light is inputted to an input portion of a first circulator 14 through an optical fiber 12b, is outputted from an input-output portion of the first circulator 14, passes through an optical fiber 12c, is outputted from an end of the optical fiber 12c, passes through a plurality of collimator lenses 15, and then enters a reference mirror 16.

The reference light reflected by the reference mirror 16, passes through the plurality of the collimator lenses 15 again, is inputted from the end of the optical fiber 12c, passes through the optical fiber 12c, and is inputted to the input-output portion of the first circulator 14. Then, the reference light outputted from an output portion of the first circulator 14 passes through an optical fiber 12d and is inputted to a first input portion of a second fiber coupler 17.

Meanwhile, the measurement light outputted from the first fiber coupler 13 is inputted to an input portion of a second circulator 18 through an optical fiber 12e. Further, the measurement light is outputted from an input-output portion of the second circulator 18, passes through an optical fiber 12f, and is outputted from an end of the optical fiber 12f. The measurement light outputted from the end of the optical fiber 12f passes through a collimator lens 19 and is inputted to a Galvano scanner 20. The Galvano scanner 20 is configured to scan the measurement light and is driven by a Galvano driver 21.

The measurement light outputted from the Galvano scanner 20 is reflected at 90 degrees by a hot minor 22 which reflects light of which wavelength is on a long-wavelength side and allows light of which wavelength is on a short-wavelength side to pass therethrough, passes through an objective lens 23, is outputted from the inspection window, and then enters the subjected eye E. The measurement light which has entered the subjected eye E is reflected at respective structural parts of the anterior eye Ec (the cornea 122, the anterior chamber, the iris 128, the crystalline lens, and the like). The reflected light therefrom enters the inspection window, and in an inverse order as the order mentioned above, passes through the objective lens 23, the hot minor 22, the Galvano scanner 20, and the collimator lens 19, and is inputted to the end of the optical fiber 12f. The reflected light inputted to the end of the optical fiber 12f passes through the optical fiber 12f, is inputted to the input-output portion of the second circulator 18, is outputted from an output portion of the second circulator 18, passes through an optical fiber 12g, and then is inputted to a second input portion of the second fiber coupler 17.

In the second fiber coupler 17, the reflected light from the anterior eye Ec inputted through the optical fiber 12g and the reference light inputted through the optical fiber 12d are multiplexed, for example at a ratio of 50:50, and a signal thereof passes through an optical fiber 12h and an optical fiber 12i, and is inputted to a detector 24. In the detector 24, interference of every wavelength is measured. The measured interference signals are inputted to an AD board 25 provided in the controller 3. Further, in a calculator 26 provided in the controller 3, processing such as Fourier transform is executed to the interference signals, and then tomographic images of the anterior eye Ec along scan lines are acquired.

A scanning pattern of the measurement light in the Galvano scanner 20, a direction of the scan lines (B-scan) in other words, is set in the controller 3. That is, the Galvano driver 21 controls the Galvano scanner 20 according to a command signal from the controller 3 (the calculator 26). Data of the acquired tomographic images of the anterior eye Ec is stored in the memory 10 after necessary refraction correction has been performed. Further, as shown in FIG. 1 schematically, a tomographic image T can be displayed on the monitor 7.

The anterior eye image capturing system 6 includes two illumination light sources 27, the objective lens 23, the hot minor 22, a cold minor 28, an imaging lens 29, a CCD camera 30, and an optical controller 31. The two illumination light sources 27 are configured to irradiate illumination light within a visible light range to a front surface of the subjected eye E. The light reflected by the subjected eye E is inputted to the CCD camera 30 from the inspection window through the objective lens 23, the hot mirror 22, the cold minor 28, and the imaging lens 29. Due to this, the front image F of the subjected eye E is captured. Data of the captured image is image-processed by the optical controller 31, and then displayed on the monitor 7.

The alignment optical system 4 includes a vision-fixation lamp optical system, an XY directional position detecting system, and a Z directional position detecting system. The vision-fixation lamp optical system is for suppressing a movement of the eyeball (subjected eye E) as much as possible by making the subject stare at a vision-fixation lamp. The XY directional position detecting system is for detecting positions of a corneal apex of the subjected eye E in X and Y directions (positional displacements in the up-and-down direction and the right-and-left direction relative to the main body). The Z directional position detecting system is for detecting a position of the corneal apex of the subjected eye E in the front-and-rear direction (Z direction).

The vision-fixation lamp optical system includes a vision-fixation lamp 32, a cold mirror 33, a relay lens 34, a half mirror 35, the cold mirror 28, the hot mirror 22, the objective lens 23, and the like. Due to this, light outputted from the vision-fixation lamp 32 (for example, green light) is irradiated toward the subjected eye E from the inspection window by passing through the cold mirror 33, the relay lens 34, the half mirror 35, the cold mirror 28, the hot mirror 22, and the lens 23 in this order.

The XY directional position detecting system includes an XY position detecting light source 36, the cold mirror 33, the relay lens 34, the half mirror 35, the cold mirror 28, the hot mirror 22, the objective lens 23, an imaging lens 37, a position sensor 38, and the like. Alignment light for position detection is outputted from the XY position detecting light source 36. The alignment light is irradiated toward the anterior eye Ec (the cornea 122) of the subjected eye E by passing through the cold mirror 33, the relay lens 34, the half mirror 35, the cold mirror 28, the hot mirror 22, the objective lens 23, and the inspection window.

Since a surface of the cornea 122 of the subjected eye E has a spherical shape, the alignment light is reflected on the surface of the cornea 122 so as to form a bright point image on an inner side of the corneal apex of the subjected eye E. The reflected light (bright point) from the surface of the cornea 122 enters from the inspection window. The reflected light from the corneal apex is inputted to the position sensor 38 by passing through the objective lens 23, the hot mirror 22, the cold mirror 28, the half mirror 35, and the imaging lens 37. A position of the bright point is detected by the position sensor 38. Due to this, a position of the corneal apex (positions in X and Y directions) is detected. The bright point is displayed on the image captured by the CCD camera 30 (the image displayed on the monitor 7) as well.

A detection signal of the position sensor 38 is inputted to the controller 3 via the optical controller 31. At this occasion, the position sensor 38 and the anterior eye image capturing system 6 (the CCD camera 30 and the monitor 7) are aligned with each other, and at the same time, a predetermined (regular) image acquiring position of the corneal apex (a position to be followed upon acquiring tomographic images) is set. For example, a point that is coincident with a center position of the image captured by the CCD camera 30 (a center position of the screen of the monitor 7) is regarded as the regular image acquiring position of the corneal apex. The controller 3 finds a positional displacement amount of the detected corneal apex (bright point) in the X direction and the Y direction (a positional displacement amount from the center of the screen of the monitor 7) relative to the regular image acquiring position based on the detection by the position sensor 38.

The Z directional position detecting system includes a Z position detecting light source 39, an imaging lens 40, and a line sensor 41. The Z position detecting light source 39 irradiates light for detection (slit light or spot light) to the subjected eye E obliquely relative to the subjected eye E. The light reflected obliquely by the cornea 122 enters the line sensor 41 through the imaging lens 40. Depending on a position of the subjected eye E in the front-and-rear direction (Z direction) relative to the main body, an incident position of the reflected light which enters the line sensor 41 varies. Due to this, by detecting the incident position, the position (distance) of the subjected eye E in the Z direction relative to the main body is detected.

A detection signal of the line sensor 41 is inputted to the controller 3 via the optical controller 31. In the controller 3, an appropriate position (distance) of the subjected eye E (the cornea 122) in the Z direction relative to the main body has been predetermined. Due to this, based on the detection by the line sensor 41, a displacement amount of the subjected eye E in the Z direction relative to the appropriate position can be obtained.

Based on the positional displacement amount of the corneal apex (bright point) in the X direction and the Y direction detected by the XY directional position detecting system and the positional displacement amount of the subjected eye E in the Z direction detected by the Z directional position detecting system, the controller 3 controls the main body driver 2 and moves the main body relative to the holding table so that those positional displacement amounts become zero. The controller 3 is configured to move the main body relative to the holding table so as to make the position of the corneal apex coincident with the predetermined image acquiring position at a time of starting to acquire tomographic images. Further, the controller 3 moves the main body so as to track the corneal apex so that a positional relationship between the corneal apex and the main body is maintained constant while tomographic images are being acquired as well. Due to this, the alignment unit and the auto eye tracking unit are constituted.

Figure 3:
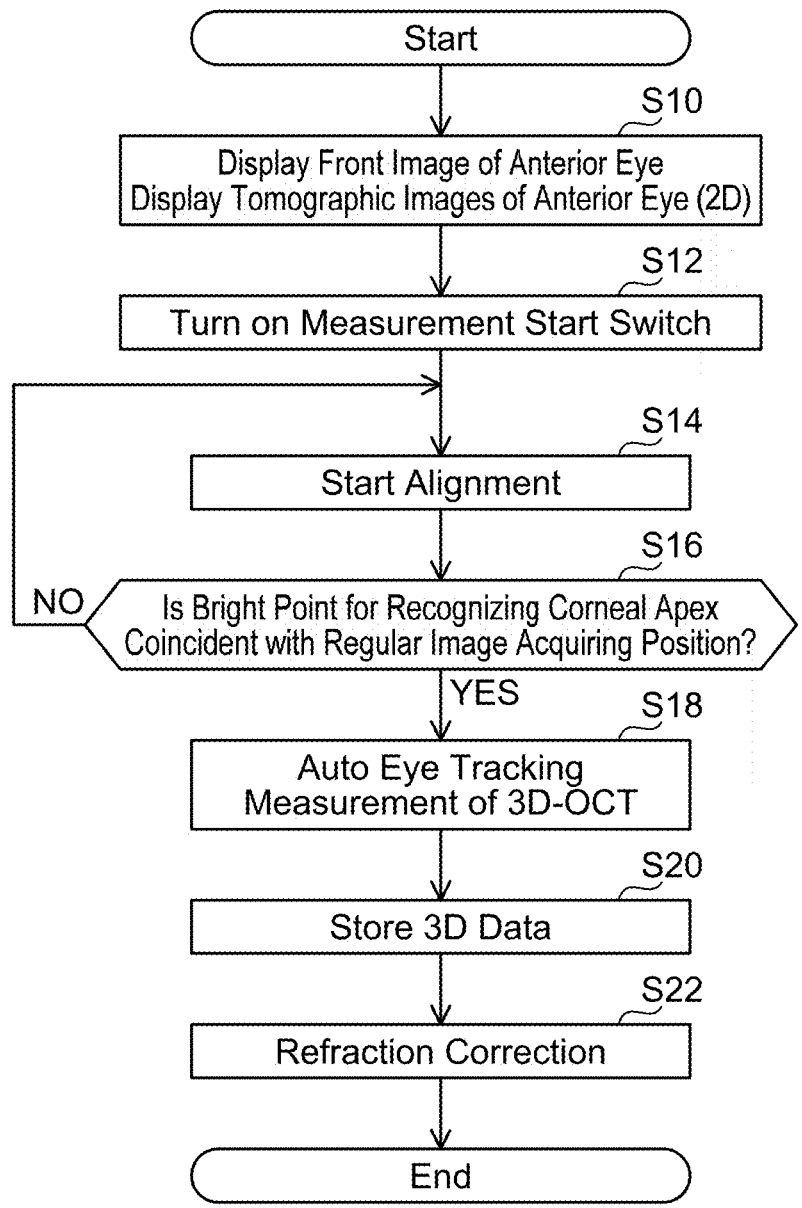
FIG. 3 is a flow chart showing an example of a procedure for measuring a shape of an anterior eye of a subjected eye using the ophthalmic apparatus of the first embodiment.

Next, a procedure for measuring the shape of the anterior eye Ec of the subjected eye E using the anterior eye OCT apparatus 1 will be described. A flowchart in FIG. 3 shows a process procedure executed by the controller 3 when tomographic images of the anterior eye Ec of the subjected eye E are captured.

The processing for capturing tomographic images of the anterior eye Ec is started (an anterior eye tomographic image capturing program is initiated) under a state where the subject puts the chin on the chin support as well as puts the forehead against the forehead pad, and the subjected eye E is positioned in front of the inspection window of the main body. First, in step S10, the controller 3 displays on the monitor 7 a current front image F of the subjected eye E which has been captured by the anterior eye image capturing system 6 (the CCD camera 30) as well as a current tomographic image T of the anterior eye Ec which has been scanned along a scan line extending horizontally and passing through the center of the screen (see FIG. 1). However, at this point of time, data of the front image F and data of the tomographic image T are not imported into the memory.

Upon detecting that the examiner has turned on the measurement start switch (step S12), the controller 3 starts alignments in the X, Y, Z directions by the alignment optical system 4 and the like in step S14. When the bright point for corneal apex recognition is not coincident with the regular image acquiring position (NO in step S16), the controller 3 returns to step S14 to perform the alignments again. When the bright point for corneal apex recognition is coincident with the regular image acquiring position (YES in step S16), the controller 3 finishes the alignments. Then, in step S18, the controller 3 executes acquisition process of tomographic images of the anterior eye Ec by the OCT system 5. During the acquisition process of the tomographic images, the auto eye-tracking functions, and thus the main body is moved by the alignment optical system 4 and the like so that the bright point for the corneal apex recognition is constantly coincident with the regular image acquiring position (a center position of the image captured by the CCD camera 30).

Figure 4A:
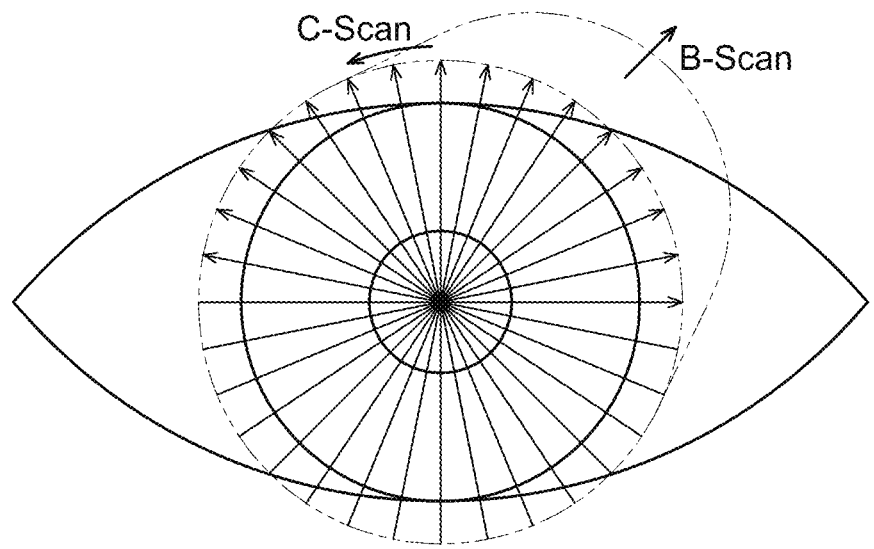
FIG. 4A is a diagram for explaining a radial scan method in an OCT.
Figure 4B:
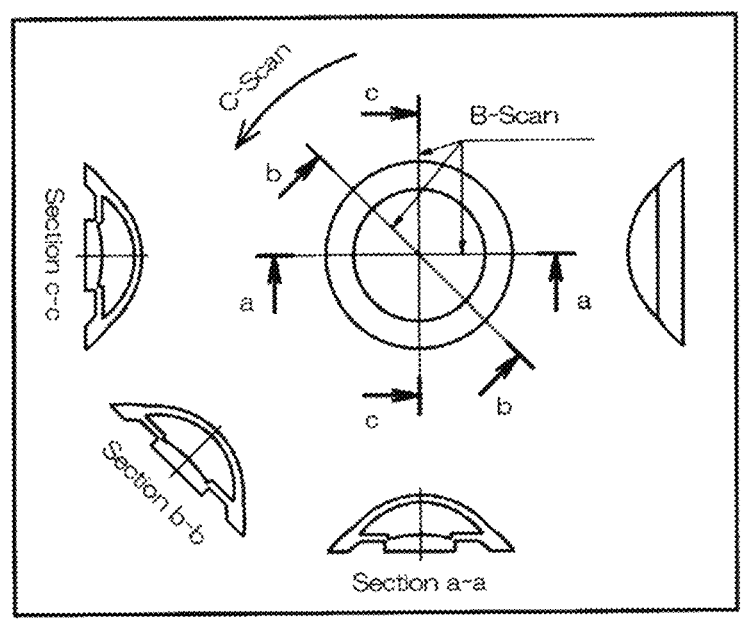
FIG. 4B is another diagram for explaining the radial scan method in the OCT.

In the present embodiment, the acquisition process of the tomographic images in step S18 is executed by a radial scan method shown in FIGS. 4A and 4B. Due to this, the tomographic images of an entire region of the anterior eye Ec are acquired. That is, the tomographic images are imported with a B-scan direction as a radial direction and a C-scan direction as a circumferential direction. At this occasion, even if the subjected eye E moves, the positional relationship between the main body and the subjected eye E is maintained constant by the auto eye tracking. Due to this, it is possible to prevent the scan lines from deviating from straight lines passing through the corneal apex. In the present embodiment, sixteen tomographic images are imported in step S18, however, no limitation is made to this configuration. The number of tomographic images acquired by the radial scan may be more than sixteen, or may be less than sixteen. In step S20, the controller 3 imports data of the acquired (captured) tomographic images into the memory.

In step S22, the controller 3 performs refraction correction process on the data of each tomographic image. Since the measurement light is refracted at the cornea 122 having a substantially spherical shape (at a boundary between the surface of the cornea 122 and the anterior chamber), the crude tomographic images have distortions. Thus, correction is performed on the image data for the cornea refraction. The image data subjected to the refraction correction process is stored in the memory 10.

Next, a process for comparing and evaluating a preoperative shape of the subjected eye E and a postoperative shape of the subjected eye E performed by the ophthalmic apparatus of the present embodiment will be described. To perform this process, firstly two-dimensional tomographic images of the subjected eye E are acquired before a surgery according to the aforementioned procedure, and two-dimensional tomographic images of the subjected eye E are acquired after the surgery according to the aforementioned procedure. The two-dimensional tomographic images acquired respectively before and after the surgery are stored in the memory 10. Then, a displacement between a reference axis which indicates a vision fixation direction of the preoperative subjected eye E obtained from the acquired preoperative two-dimensional tomographic images and a reference axis which indicates a vision fixation direction of the postoperative subjected eye E obtained from the acquired postoperative two-dimensional tomographic images is corrected. Then, the preoperative and postoperative two-dimensional tomographic images of which displacement in their reference axes has been corrected are compared to evaluate a shape change in the subjected eye E before and after the surgery. Firstly, a procedure for correcting the displacement in the reference axes will be described in detail. For example, the shape of the subjected eye E changes before and after a cataract surgery. In order to evaluate this shape change with high accuracy, the reference axis indicating the vision fixation direction of the subjected eye E in the preoperatively acquired two-dimensional tomographic images and the reference axis indicating the vision fixation direction of the subjected eye E in the postoperatively acquired two-dimensional tomographic images need to be matched to each other. Upon acquiring the two-dimensional tomographic images, a subject is instructed to stare at the vision-fixation lamp so that visual axes are matched to each other. However, due to a deteriorated vision before the surgery, the axes of the vision fixation directions in the acquired two-dimensional tomographic images may be displaced. In the present embodiment, the displacement between the reference axis of the vision fixation direction of the preoperative subjected eye E and the reference axis of the vision fixation direction of the postoperative subjected eye E is corrected based on a scleral spur SS. In the present embodiment, the axis of the vision fixation direction of the subjected eye E is used as the reference axis, however, no limitation is made to this configuration. Any axis that can be obtained by same configurations in the preoperative subjected eye E and the postoperative subjected eye E, and with which the preoperative subjected eye E and the postoperative subjected eye E can be matched after the displacement correction can be used as the reference axis.

Figure 6:
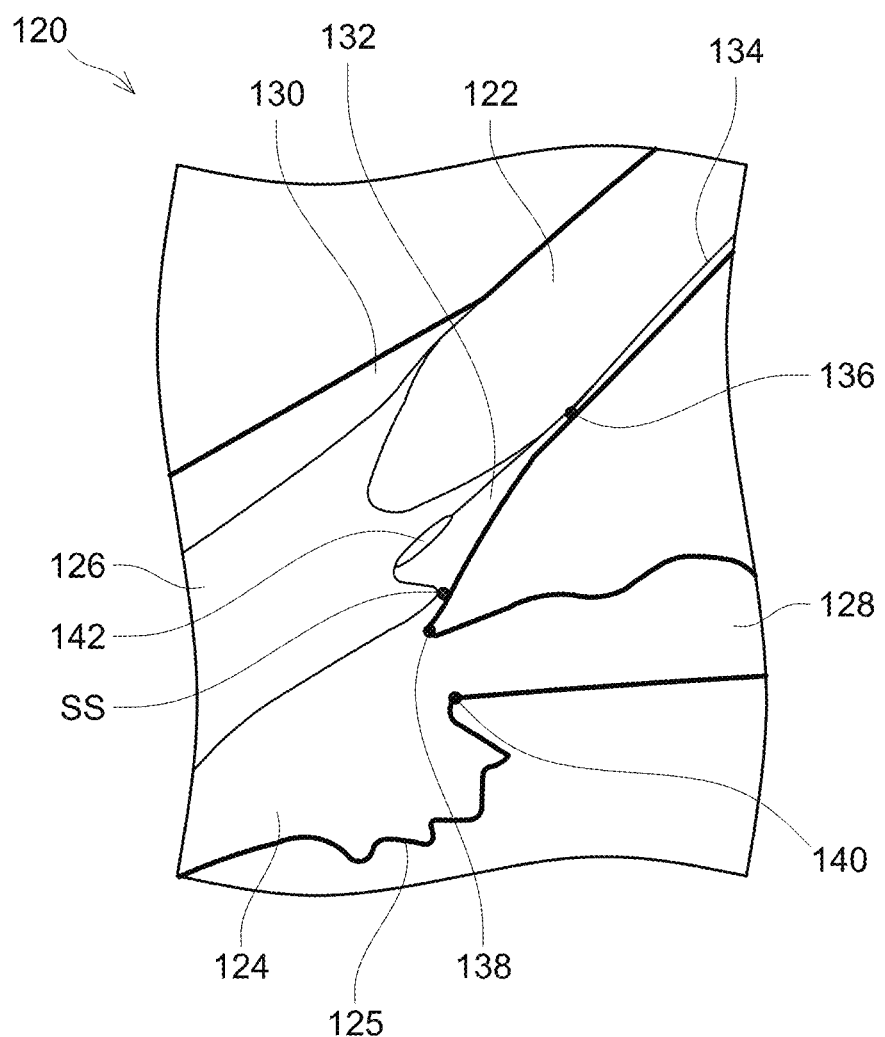
FIG. 6 is a diagram showing an angle of an anterior chamber of the subjected eye.

A procedure for correcting the displacement between the reference axis of the preoperative subjected eye E and the reference axis of the postoperative subjected eye E based on the scleral spur SS will be described. As shown in FIG. 6, the scleral spur SS is located in an angle 120 of an anterior chamber, and is located at a boundary between a trabecula 132, a ciliary body 124, and a sclera 126. The scleral spur SS is known to be resistant to shape change before and after the cataract surgery and the like. Due to this, a position of the scleral spur SS is used as a reference to calculate a displacement amount between the reference axis of the preoperative subjected eye E and the reference axis of the postoperative subjected eye E.

As shown in FIG. 5, firstly, the calculator 26 acquires the two-dimensional tomographic images of the preoperative subjected eye E and the two-dimensional tomographic images of the postoperative subjected eye E from the memory 10 (S30). That is, the calculator 26 acquires sixteen two-dimensional tomographic images of the preoperative subjected eye E calculated by the aforementioned radial scan from the memory 10. Similarly, the calculator 26 acquires sixteen two-dimensional tomographic images of the postoperative subjected eye E calculated by the aforementioned radial scan from the memory 10.

Next, the position of the scleral spur SS is detected for each of the two-dimensional tomographic images of the preoperative subjected eye E and each of the two-dimensional tomographic images of the postoperative subjected eye E (S32). The position of the scleral spur SS is detected by a point input inputted by an examiner to each two-dimensional tomographic image using an input device (not shown) such as a mouse. Thus, the examiner identifies the position of the scleral spur SS for each of the sixteen two-dimensional tomographic images of the preoperative subjected eye E, and further identifies the position of the scleral spur SS for each of the sixteen two-dimensional tomographic images of the postoperative subjected eye E. In the present embodiment, the positions of the scleral spur SS are detected by the identifying performed by the examiner, however, the positions of the scleral spur SS may be detected by the calculator 26 executing an image processing program, and thus no limitation is made to the configuration of the present embodiment.

Figure 7:
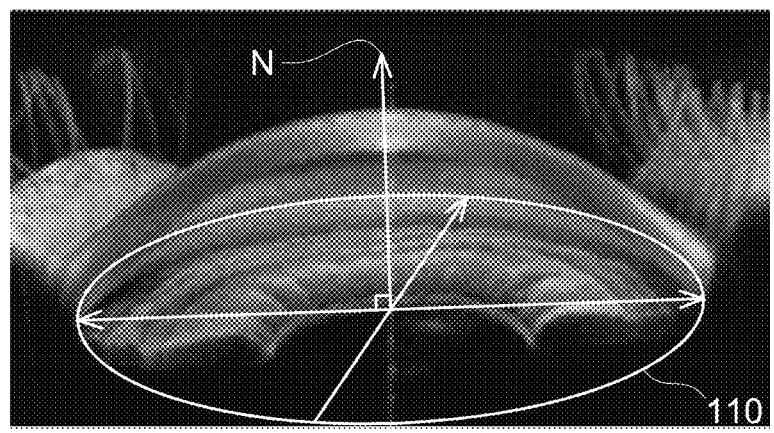
FIG. 7 is a diagram showing an approximate circle of the scleral spur of the subjected eye.

When the positions of the scleral spur SS are detected, the calculator 26 constructs three-dimensional images of the subjected eye E based on the plurality of two-dimensional tomographic images stored in the memory 10 (S34). Specifically, as shown in FIG. 7, the calculator 26 constructs a three-dimensional image of the preoperative subjected eye E from the sixteen two-dimensional tomographic images of the preoperative subjected eye E acquired by the radial scan. Similarly, the calculator 26 constructs a three-dimensional image of the postoperative subjected eye E from the sixteen two-dimensional tomographic images of the postoperative subjected eye E acquired by the radial scan.

When the three-dimensional images are constructed, the calculator 26 calculates approximate circles 110 expressing the scleral spur SS (S36). That is, the calculator 26 calculates the approximate circles 110 expressing the scleral spur SS by subjecting the thirty-two points indicating the positions of the scleral spur SS detected in step S32 to curve approximation. The shapes calculated by the curve approximation may be a circle or may be an ellipse, depending on the subjected eye E, however in the present embodiment, both shapes that are close to a circle and close to an ellipse will be termed "approximate circle of the scleral spur SS". In step S36, the approximate circle of the scleral spur SS is calculated for each of the preoperative subjected eye E and the postoperative subjected eye E.

When the approximate circles 110 of the scleral spur SS are calculated, the calculator 26 calculates a normal vector N of each approximate circle 110 of the scleral spur SS and a coordinate of a center of each approximate circle 110 of the scleral spur SS (S38). The calculator 26 calculates the normal vector N and the center coordinate of the approximate circle 110 for each of the preoperative subjected eye E and the postoperative subjected eye E. In the present embodiment, axes matching the normal vectors N are regarded as the reference axes.

When the normal vectors N and the center coordinates of the scleral spur SS are calculated, the calculator 26 moves (positionally correct) the approximate circle 110 of the scleral spur SS of the preoperative subjected eye E such that it matches the approximate circle 110 of the scleral spur SS of the postoperative subjected eye E (S40). By matching of the scleral spurs SS, of which shape hardly changes before and after the surgery, the displacement between the reference axis of the preoperative subjected eye E and the reference axis of the postoperative subjected eye E can be corrected. In the present embodiment, the position of the scleral spur SS of the preoperative subjected eye E is corrected to match the scleral spur SS of the postoperative subjected eye E, however, no limitation is made to this configuration. For example, the position of the scleral spur SS of the postoperative subjected eye E may be corrected to match the scleral spur SS of the preoperative subjected eye E, or both of the positions of the scleral spur SS of the preoperative subjected eye E and of the scleral spur SS of the postoperative subjected eye E may be corrected to match with each other.

In the present embodiment, the displacement between the reference axis of the vision fixation direction of the preoperative subjected eye E and the reference axis of the vision fixation direction of the postoperative subjected eye E is corrected based on the scleral spur SS, however, no limitation is made to this configuration. Any portion that is resistant against shape change before and after the cataract surgery and the like may be used as the reference for calculating the displacement amount between the reference axis of the preoperative subjected eye E and the reference axis of the postoperative subjected eye E. For example, a Schwalbe 136, an angle recess 138, a ciliary body groove 140, and a center of a Schlemm's canal 142 located within the angle 120 of the anterior chamber as shown in FIG. 6 may be used instead of the scleral spur SS. The Schwalbe 136 is located at a boundary between an endothelium of the cornea 122, an end portion of a Descemet membrane 134 at an edge of the cornea 122, and a front edge of the trabecula 132. The angle recess 138 is located at a boundary between a rear surface of the cornea 122, the ciliary body 124, and a front surface of the iris 128. The ciliary body groove 140 is located at a boundary between a rear surface of the iris 128 and a ciliary body protrusion 125. The Schlemm's canal 142 is a tubular tissue located between the trabecula 132 and the sclera 126. When the Schlemm's canal 142 is to be used, a position of the center of the Schlemm's canal 142 may be detected and used.

Further, in the present embodiment, a position in at least one of the two-dimensional tomographic images of the preoperative subjected eye E and the two-dimensional tomographic images of the postoperative subjected eye E is corrected such that the displacement between the reference axis of the preoperative subjected eye E and the reference axis of the postoperative subjected eye E is cancelled, however, no limitation is made to this configuration. For example, a displacement between a corneal shape map of the preoperative subjected eye E and a corneal shape map of the postoperative subjected eye E may be corrected based on the displacement amount between the reference axis of the preoperative subjected eye E and the reference axis of the postoperative subjected eye E which are calculated based on the two-dimensional tomographic images of the preoperative subjected eye E and the postoperative subjected eye E. Specifically, the displacement amount between the reference axis of the preoperative subjected eye E and the reference axis of the postoperative subjected eye E is calculated by the steps S30 to S38 as aforementioned. One of the corneal shape map of the preoperative subjected eye E and the corneal shape map of the postoperative subjected eye E is corrected by an amount corresponding to the displacement amount, such that the reference axis of the preoperative subjected eye E and the reference axis of the postoperative subjected eye E match with each other based on the calculated displacement amount. Both of the corneal shape map of the preoperative subjected eye E and the corneal shape map of the postoperative subjected eye E may be corrected such that the displacement between the reference axis of the preoperative subjected eye E and the reference axis of the postoperative subjected eye E is cancelled.

Figure 8:
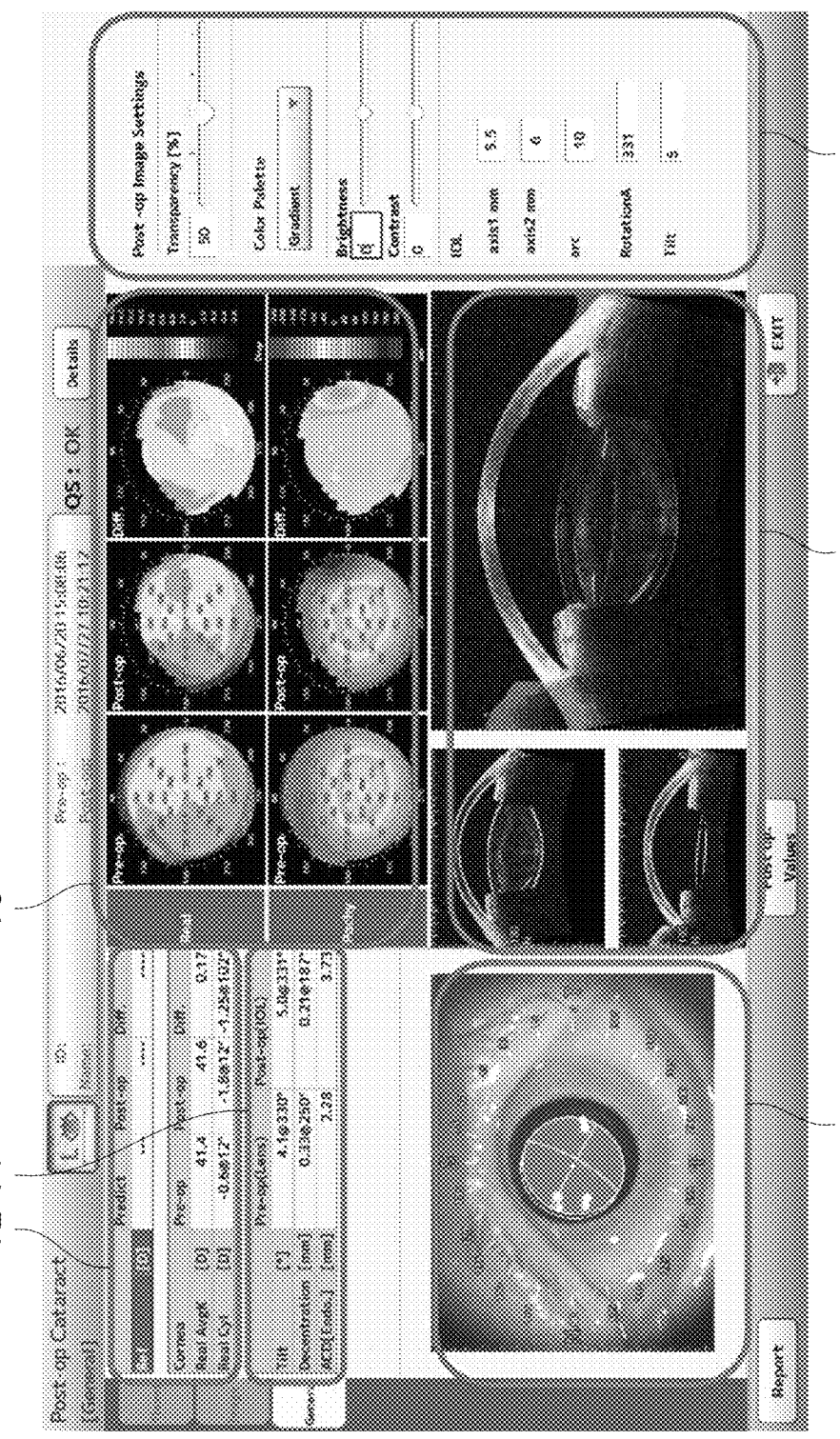
FIG. 8 is a diagram showing an example of a display screen displayed on a monitor.

When the displacement between the reference axis of the preoperative subjected eye E and the reference axis of the postoperative subjected eye E is corrected as above, the calculator 26 displays images of the preoperative subjected eye E and the postoperative subjected eye E after the correction on the monitor 7. The examiner can evaluate the shape change between the preoperative subjected eye E and the postoperative subjected eye E from the images displayed on the monitor 7. A display screen to be displayed on the monitor 7 will be described in detail with reference to the drawings. As aforementioned, when the displacement between the reference axes is corrected, the calculator 26 displays the images of the respective portions of the subjected eyes E after the correction on the monitor 7. FIG. 8 shows an example of information related to the respective portions of the subjected eyes E displayed on the monitor 7. As shown in FIG. 8, the monitor 7 displays parameter display columns 70, a corneal shape map section 76, an intraocular lens schematic diagram 78, an anterior eye tomographic image section 80, and a display setting column 82.

The parameter display columns 70 include a parameter display column 72 related to the corneal shape and a parameter display column 74 related to the crystalline lens and the intraocular lens. In the parameter display columns 70 of the present embodiment, the parameter display column 72 related to the corneal shape is arranged on an upper side with respect to the parameter display column 74 related to the crystalline lens and the intraocular lens.

The parameter display column 72 related to the corneal shape displays parameters of corneal refractive force and corneal cylinder level. In the present embodiment, the parameter of the corneal refractive force is arranged on the upper side with respect to the parameter of the corneal cylinder level. Further, the parameters of the corneal refractive force and the corneal cylinder level are displayed for each of the preoperative subjected eye E, the postoperative subjected eye E, and preoperative-postoperative difference in this order from the left side. By displaying the parameters regarding the preoperative and postoperative corneal shapes, quantitative evaluation can easily be performed.

The parameter display column 74 related to the crystalline lens and the intraocular lens displays parameters of tilt, decentration, and anterior chamber depth of the crystalline lens and the intraocular lens. In the present embodiment, the parameter related to the tilt is displayed on the upper side with respect to the parameter related to the decentration, and the parameter related to the decentration is displayed on the upper side with respect to the parameter related to the anterior chamber depth. Further, the parameters of the tilt, the decentration, and the anterior chamber depth are displayed for the preoperative crystalline lens on the left side, and for the postoperative intraocular lens on the right side. The parameters related to the preoperative crystalline lens and the parameters related to the postoperative intraocular lens are collectively displayed to enable easy comparison of these parameters.

The corneal shape map section 76 displays the corneal refractive force on the upper side with respect to the corneal thickness. Further, the cornea refractive force and the corneal thickness are displayed for each of the preoperative corneal shape, the postoperative corneal shape, and preoperative-postoperative difference in this order from the left side. By displaying the preoperative and postoperative corneal shapes and the difference therebetween, the preoperative and postoperative states of the cornea 122 can be evaluated visually. Further, by evaluating the cornea refractive force, a state of induced astigmatism caused by the surgery can be evaluated. By evaluating the corneal thickness, a healing state of a cornea incision provided upon inserting the intraocular lens can be evaluated. The corneal shape map section 76 is arranged on the right side with respect to the parameter display columns 70.

The intraocular lens schematic diagram 78 schematically displays a state of the intraocular lens based on the parameter display related to the intraocular lens. By schematically displaying the state of the intraocular lens, a direction toward which the intraocular lens is tilted can easily be recognized visually and be evaluated. The intraocular lens schematic diagram 78 is arranged below the parameter display columns 70.

The anterior eye tomographic image section 80 displays tomographic images of the anterior eye Ec of the preoperative and postoperative subjected eyes E vertically on its left side, and displays an image in which the tomographic images of the anterior eye Ec of the preoperative and postoperative subjected eyes E are superimposed over one another on its right side. By displaying the image showing the state where the aforementioned tomographic images are superimposed over one another, the change in the shapes before and after the surgery can easily be evaluated. Further, by displaying each of the preoperative and postoperative tomographic images together with the image in which they are superimposed over one another, accurate comparison and evaluation can be performed even for a portion whose evaluation becomes more difficult due to the superimposition. The anterior eye tomographic image section 80 is arranged below the corneal shape map section 76 and on the right side with respect to the intraocular lens schematic diagram 78.

The display setting column 82 displays various settings related to the screen display. In the display setting column 82, for example, settings related to transparency, color pallet, brightness, contrast, and the like may be performed. The display setting column 82 is arranged on the right side of the monitor 7.

On the monitor 7, the parameter display column 72 related to the corneal shape and the corneal shape map section 76 are arranged at an upper portion of the screen, and the parameter display column 74 related to the crystalline lens and the intraocular lens, the intraocular lens schematic diagram 78, and the anterior eye tomographic image section 80 are arranged at a lower portion of the screen. That is, the displays related to the corneal shape are arranged to gather at the upper portion of the screen, and the displays related to the crystalline lens and the intraocular lens are arranged to gather at the lower portion of the screen. Due to this, the information on the corneal shape, which greatly influences visual function of the subjected eye E after the cataract surgery and the like, and the information related to the crystalline lens and the intraocular lens can easily be evaluated visually. Further, by displaying the parameter display columns 70, the corneal shape map section 76, the intraocular lens schematic diagram 78, and the anterior eye tomographic image section 80 at the same time, the changes in the shapes of the cornea 122 and the crystalline lens and the intraocular lens, as well as the intraocular position of the crystalline lens and the intraocular lens can more easily be evaluated. The monitor 7 may display the shape of the angle 120 of the anterior chamber of the preoperative subjected eye E and the shape of the angle 120 of the anterior chamber of the postoperative subjected eye E.

When the aforementioned analysis is completed, the calculator 26 stores an analysis result in the memory 10. The analysis result stored in the memory 10 may include not only the analysis result displayed on the monitor 7 as aforementioned but also analysis result(s) that is not displayed on the monitor 7. As such analysis result(s) to be stored in the memory 10, for example, evaluation results of change between the preoperative subjected eye E and the postoperative subjected eye E in regard to radii of curvatures of the front and rear surfaces of the cornea 122, the corneal thickness distribution, the anterior chamber depth, the tilt of the intraocular lens, an axial length, and the like may be exemplified. The subjected eye E after the cataract surgery and the like may have been changed in the radii of curvatures of the front and rear surfaces of the cornea 122, the corneal thickness distribution, the anterior chamber depth, the tilt of the intraocular lens, the axial length, and the like, due to the influence of the surgery and the like. The calculator 26 stores these analysis results in the memory 10, and can predict a shape change that would be caused by the cataract surgery and the like based on the stored analysis results. For example, a shape measurement for an eye to be operated is performed before the surgery, and based on the measurement result thereof, eye data including a preoperative eye shape similar to the shape of the eye to be operated (preoperative and postoperative eye shapes and analysis results thereof) is identified from the memory 10. Further, the shape of the eye to be operated after the surgery is predicted from the shape of the eye to be operated measured before the surgery and the eye data identified from the memory 10 (especially, the postoperative eye shape and a preoperative-postoperative change amount). By accumulating the analysis results in the memory 10, a morphological change in the postoperative subjected eye E can be predicted accurately from the shape of the preoperative subjected eye E. Due to this, for example, accuracy of calculation for power of the intraocular lens can be improved.

The ophthalmic apparatus of the present embodiment calculates the displacement amount between the reference axis indicating the vision fixation direction of the preoperative subjected eye E and the reference axis indicating the vision fixation direction of the postoperative subjected eye E, and corrects at least one of the reference axis of the preoperative subjected eye E and the reference axis of the postoperative subjected eye E based on the calculated displacement amount. Especially in the preoperative subjected eye E, there is a case where staring at the vision-fixation lamp is difficult due to the deteriorated vision. Even in such a case, the displacement between the vision fixation directions can be corrected after the acquisition of the two-dimensional tomographic images, so the shape change between the preoperative subjected eye E and the postoperative subjected eye E can suitably be evaluated.

Further, the ophthalmic apparatus of the present embodiment displays, on the monitor 7, the shapes of the respective portions of the subjected eye E after the correction of the displacement between the reference axis of the preoperative subjected eye E and the reference axis of the postoperative subjected eye E. Due to this, the shape changes in the respective portions of the preoperative and postoperative subjected eyes E can accurately be evaluated. Further, the monitor 7 displays the preoperative shape, the postoperative shape, and the difference in the shape changes thereof for the respective portions of the subjected eye E such that they are arranged adjacent to each other. Alternatively, the monitor 7 may display the preoperative shape and the postoperative shape by superimposing them over one another, instead of displaying the difference of the shape change. Due to this, the shape change before and after the surgery can easily be recognized.

Further, the ophthalmic apparatus of the present embodiment stores the information related to the preoperative-postoperative shape change in the memory 10. That is, it can store the analysis results of the preoperative-postoperative shape change. Due to this, the postoperative shape can be predicted from the preoperative shape, and the prediction accuracy can be increased with a greater collection of the analysis results. Due to this, for example, the accuracy of the calculation for the power of the intraocular lens can be improved.

Second Embodiment

In the aforementioned first embodiment, the displacement between the reference axis of the preoperative subjected eye E and the reference axis of the postoperative subjected eye E is corrected based on the shape of the scleral spur SS, however, no limitation is made to this configuration. So long as a tissue is resistant against the shape change before and after the surgery, the displacement between the reference axes can be corrected based on a shape of the tissue. In a second embodiment, a procedure for correcting the displacement between the reference axis of the preoperative subjected eye E and the reference axis of the postoperative subjected eye E based on the corneal shape will be described. The second embodiment differs from the first embodiment in its configuration for correcting the displacement between the reference axes of the preoperative and postoperative subjected eyes E based on the corneal shape, and other configurations thereof are substantially same as those of the first embodiment. Thus, the description of the configurations other than the configuration for correcting the displacement between the reference axes will be omitted.

Figure 9:
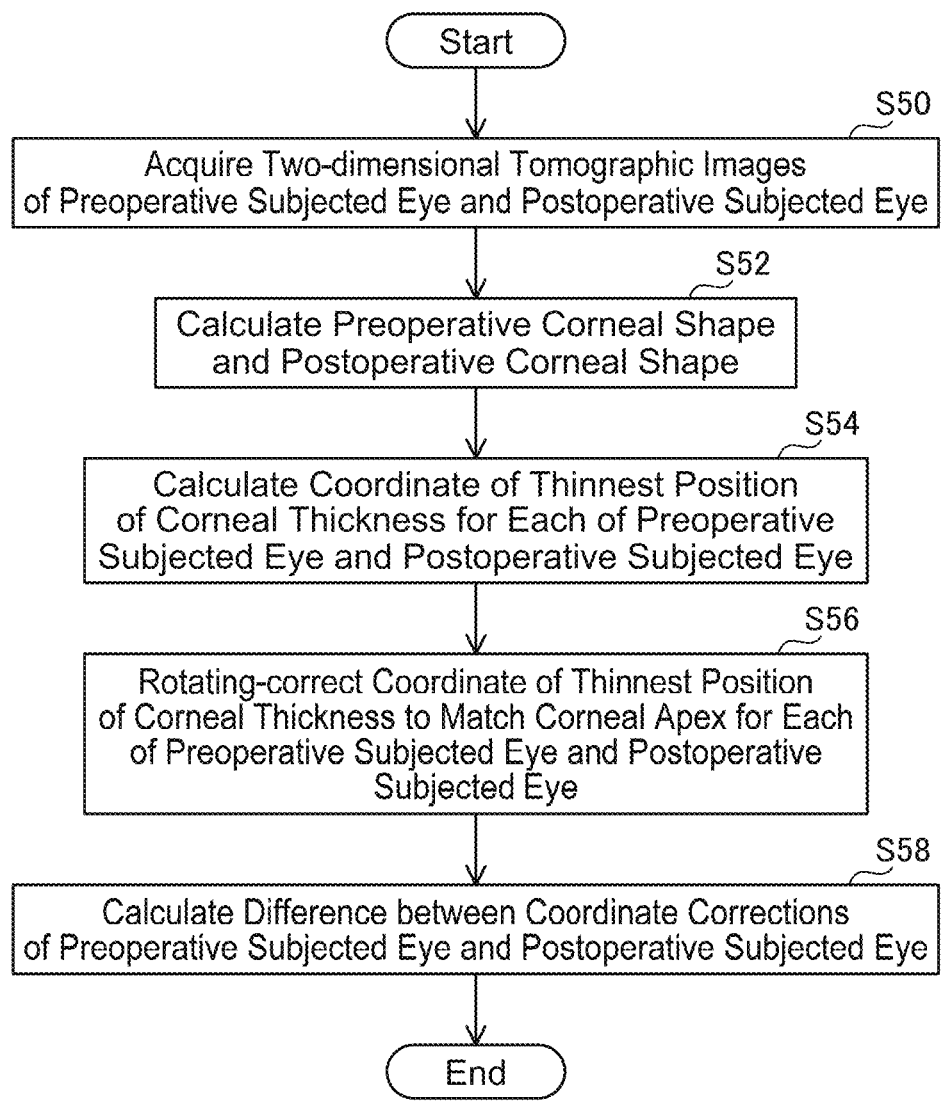
FIG. 9 is a flow chart showing an example of a procedure for correcting a displacement amount based on a corneal shape using an ophthalmic apparatus of a second embodiment.

As shown in FIG. 9, firstly, the calculator 26 acquires the two-dimensional tomographic images of the preoperative subjected eye E and the two-dimensional tomographic images of the postoperative subjected eye E from the memory 10 (S50). Since step S50 is the same step as step S30 as aforementioned, so details thereof will be omitted.

Next, the calculator 26 calculates the preoperative corneal shape and the postoperative corneal shape of the subjected eye E (S52). The calculator 26 calculates the corneal shape of the preoperative subjected eye E from each of the sixteen two-dimensional tomographic images of the preoperative subjected eye E. Specifically, for each of the two-dimensional tomographic images, the corneal thickness is calculated from positional information of the front and rear surfaces of the cornea 122. The calculation of the corneal thickness is performed for plural points including an apex of the cornea 122 in each two-dimensional tomographic image. For example, the corneal thickness is calculated for plural points arranged at predetermined intervals from the apex of the cornea 122. Then, the calculator 26 uses the corneal thicknesses calculated respectively for the sixteen two-dimensional tomographic images of the preoperative subjected eye E to calculate a corneal thickness map (see FIG. 10) indicating the corneal thickness distribution of the preoperative subjected eye E. As it is apparent from FIG. 10, the corneal thickness map represents a two-dimensional distribution of the corneal thickness in a front view of the subjected eye E. Similarly, the calculator 26 calculates a corneal thickness map of the postoperative subjected eye E based on the sixteen two-dimensional tomographic images of the postoperative subjected eye E.

When the corneal shapes (that is, the corneal thickness maps (FIG. 10)) of the preoperative and postoperative subjected eyes E are calculated, the calculator 26 calculates a coordinate of a portion (thinnest position) 103 where the corneal thickness is the thinnest in the preoperative subjected eye E from the corneal thickness map of the preoperative subjected eye E (S54). In the cornea 122, the corneal thickness at the apex is the thinnest. Due to this, the calculated thinnest position 103 can be assumed as being at the apex of the cornea 122. Similarly, the calculator 26 calculates a coordinate of a thinnest position 103 of the corneal thickness of the postoperative subjected eye E from the corneal thickness map of the postoperative subjected eye E.

Figures 10, 11:
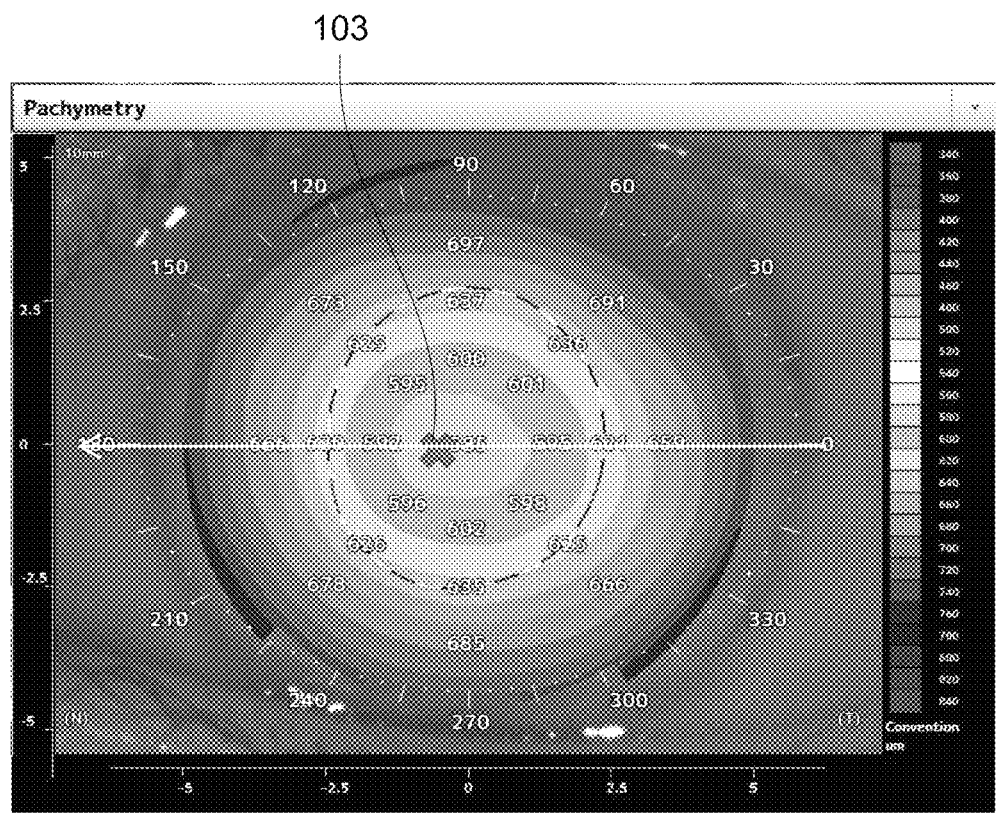
FIG. 10 is a corneal thickness map showing a corneal thickness distribution of a subjected eye.
FIG. 11 is a cross sectional view showing a cornea and a ciliary body of the subjected eye.

Next, the calculator 26 performs a rotating correction so that the thinnest position 103 is arranged at a center 200 of the corneal thickness map (S56). As shown in FIG. 11, if the reference axis indicating the vision fixation direction of the subjected eye E is displaced, the thinnest position 103 is displaced from the center 200 by the displacement amount of the reference axis. Due to this, by performing the rotating correction to match the thinnest position 103 to the center 200 of the corneal thickness map, the displacement in the reference axis of the subjected eye E can be corrected. This correction is performed for the preoperative subjected eye E as well as for the postoperative subjected eye E. That is, the thinnest position 103 of the preoperative subjected eye E is arranged at the center 200 of the corneal thickness map. Further, the thinnest position 103 of the postoperative subjected eye E is also arranged at the center 200 of the corneal thickness map.

Finally, the calculator 26 calculates a difference between the coordinate corrections of the preoperative subjected eye E and the postoperative subjected eye E (S58). That is, a difference between the thinnest position 103 of the corneal thickness of the preoperative subjected eye E that was corrected in step S56 and the thinnest position 103 of the corneal thickness of the postoperative subjected eye E that was corrected in step S56 is calculated. This difference is stored in the memory 10 as the displacement amount between the preoperative subjected eye E and the postoperative subjected eye E. By using the stored difference (displacement amount), the preoperative and postoperative two-dimensional tomographic images can be corrected to their correct positions. In the present embodiment, the thinnest position 103 of the corneal thickness of the preoperative subjected eye E is corrected to the center 200, and the thinnest position 103 of the corneal thickness of the postoperative subjected eye E is corrected to the center 200, however, no limitation is made to this configuration. For example, the coordinate of the thinnest position 103 of the corneal thickness of the postoperative subjected eye E may be corrected to match the coordinate of the thinnest position 103 of the corneal thickness of the preoperative subjected eye E, or the coordinate of the thinnest position 103 of the corneal thickness of the preoperative subjected eye E may be corrected to match the coordinate of the thinnest position 103 of the corneal thickness of the postoperative subjected eye E. Further, the correction may be performed with a reference axis of the eye such as the visual axis, a fixation line, a line of sight, or the like as the center. Even with such methods, the reference axis of the preoperative subjected eye E and the reference axis of the postoperative subjected eye E can be matched to each other, and the shape change between the preoperative and postoperative subjected eyes E can accurately be evaluated.

Figure 12:
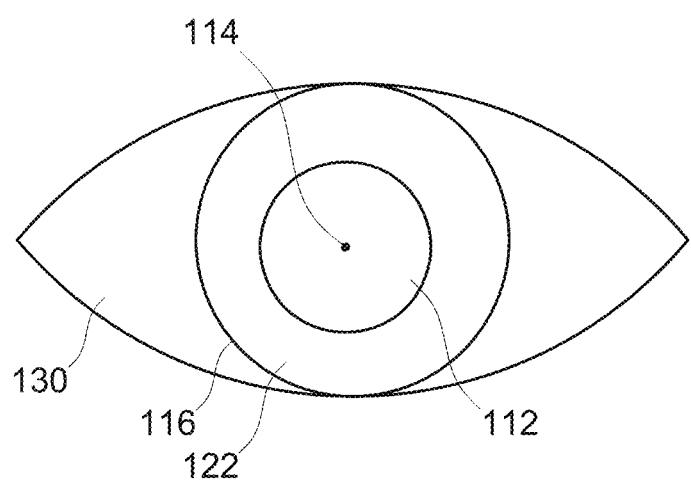
FIG. 12 is a diagram showing a pupil and a corneal limbus of the subjected eye.

In the present embodiment, the displacement between the reference axis of the preoperative subjected eye E and the reference axis of the postoperative subjected eye E is corrected based on the corneal shape, however, no limitation is made to this configuration. Any tissue that is resistant to shape deformation before and after the cataract surgery and the like can be used as the reference for calculating the displacement amount between the reference axis of the preoperative subjected eye E and the reference axis of the postoperative subjected eye E. For example, any one of the shape of a pupil 112 and the shape of a corneal limbus 116 shown in FIG. 12 may be used instead of the corneal shape. When the correction of the displacement amount is to be performed based on the shape of the pupil 112, a coordinate of a pupil center 114 is calculated from the shape of the pupil 112 for each of the preoperative subjected eye E and the postoperative subjected eye E, and the coordinates of the pupil centers 114 of the preoperative subjected eye E and the postoperative subjected eye E can be corrected. Further, when the correction of the displacement amount is to be performed based on the shape of the corneal limbus 116, a coordinate of a center of the corneal limbus 116 (not shown) is calculated from the shape of the corneal limbus 116, which is a boundary between the cornea 122 and a conjunctiva 130, for each of the preoperative subjected eye E and the postoperative subjected eye E, and the coordinates of the centers of the corneal limbi 116 of the preoperative subjected eye E and the postoperative subjected eye E can be corrected. That is, the displacement amount between the reference axis of the preoperative subjected eye E and the reference axis of the postoperative subjected eye E can be calculated by calculating the coordinates of the pupil centers 114 or the centers of the corneal limbi 116, instead of the thinnest portions 103 of the corneal thickness.

While specific examples of the present invention have been described above in detail, these examples are merely illustrative and place no limitation on the scope of the patent claims. The technology described in the patent claims also encompasses various changes and modifications to the specific examples described above. The technical elements explained in the present description or drawings provide technical utility either independently or through various combinations. The present invention is not limited to the combinations described at the time the claims are filed.

What is claimed is:

1. An ophthalmic apparatus configured to measure a shape of a subjected eye, the apparatus comprising:
    a processor;
    an anterior eye image capturing system; and
    a memory storing computer-readable instructions therein, the computer-readable instructions, when executed by the processor, causing the ophthalmic apparatus to perform:
    acquiring a preoperative two-dimensional tomographic image of a preoperative subjected eye;
    acquiring a postoperative two-dimensional tomographic image of a postoperative subjected eye;
    calculating a preoperative shape of the preoperative subjected eye based on the preoperative two-dimensional tomographic image of the preoperative subjected eye acquired by the acquiring of the preoperative two-dimensional tomographic image;
    calculating a postoperative shape of the postoperative subjected eye based on the postoperative two-dimensional tomographic image of the postoperative subjected eye acquired by the acquiring of the postoperative two-dimensional tomographic image; and
    calculating a displacement amount between a first line of reference obtained from the preoperative two-dimensional tomographic image of the preoperative subjected eye and a second line of reference obtained from the postoperative two-dimensional tomographic image of the postoperative subjected eye, based on the calculated preoperative shape and the calculated postoperative shape,
    wherein each of the first and second lines of reference is a normal vector of an approximate circle calculated from an internal shape of a corresponding one of the preoperative subjected eye and the postoperative subjected eye.

2. The ophthalmic apparatus according to claim 1, wherein
    the internal shape includes at least one of a shape of an angle of an anterior chamber, a corneal shape, a corneal limbus shape, and a pupil shape.

3. The ophthalmic apparatus according to claim 2, wherein
    the computer-readable instructions further cause the ophthalmic apparatus to perform correcting at least one of the preoperative two-dimensional tomographic image and the postoperative two-dimensional tomographic image based on the calculated displacement amount to match the first line of reference of the preoperative subjected eye and the second line of reference of the postoperative subjected eye to each other.

4. The ophthalmic apparatus according to claim 3, wherein
    the computer-readable instructions further cause the ophthalmic apparatus to perform calculating a positional displacement amount at a preset portion of the subjected eye before and after a surgery by comparing the preoperative two-dimensional tomographic image and the postoperative two-dimensional tomographic image, one of or both of which have been corrected in the correcting of at least one of the two-dimensional tomographic images,
    the memory is further configured to store information related to the positional displacement amount calculated in the calculating of the positional displacement amount, and
    the computer-readable instructions further cause the ophthalmic apparatus to perform predicting a shape of the postoperative subjected eye based on the preoperative two-dimensional tomographic image of the preoperative subjected eye acquired by the acquiring of the two-dimensional tomographic image and the information related to the positional displacement amount stored in the memory.

5. The ophthalmic apparatus according to claim 3, wherein
    the computer-readable instructions further cause the ophthalmic apparatus to perform displaying information related to the preoperative shape of the subjected eye, information related to the postoperative shape of the subjected eye, and the information related to the displacement amount.

6. The ophthalmic apparatus according to claim 5, wherein
    the information related to the preoperative shape of the subjected eye is the preoperative two-dimensional tomographic image of the preoperative subjected eye, the information related to the postoperative shape of the subjected eye is the postoperative two-dimensional tomographic image of the postoperative subjected eye, the at least one of the preoperative two-dimensional tomographic image of the preoperative subjected eye and the postoperative two-dimensional tomographic image of the postoperative subjected eye is corrected in the correcting of at least one of the two-dimensional tomographic images, and the displaying is configured to display at least one of an image that displays the preoperative two-dimensional tomographic image of the preoperative subjected eye adjacent to the postoperative two-dimensional tomographic image of the postoperative subjected eye, and an image that displays one of the preoperative two-dimensional tomographic image of the preoperative subjected eye and the postoperative two-dimensional tomographic image of the postoperative subjected eye being superimposed over the other thereof.

7. The ophthalmic apparatus according to claim 2, wherein the computer-readable instructions further cause the ophthalmic apparatus to perform:

acquiring a corneal shape map of the subjected eye; and correcting at least one of a corneal shape map of the preoperative subjected eye and a corneal shape map of the postoperative subjected eye that are acquired by the acquiring of the corneal shape map, based on the calculated displacement amount, to match the first line of reference of the preoperative subjected eye and the second line of reference of the postoperative subjected eye to each other.

8. The ophthalmic apparatus according to claim 7, wherein the computer-readable instructions further cause the ophthalmic apparatus to perform displaying at least one of an image that displays the corneal shape map of the preoperative subjected eye and the corneal shape map of the postoperative subjected eye, one of or both of which have been corrected by the correcting of the at least one of the corneal shape maps, and an image that displays a differential map of the corneal shape map of the preoperative subjected eye and the corneal shape map of the postoperative subjected eye.

9. The ophthalmic apparatus according to claim 1, wherein the computer-readable instructions further cause the ophthalmic apparatus to perform correcting at least one of the preoperative two-dimensional tomographic image and the postoperative two-dimensional tomographic image based on the calculated displacement amount to match the first line of reference of the preoperative subjected eye and the second line of reference of the postoperative subjected eye to each other.

10. The ophthalmic apparatus according to claim 9, wherein the computer-readable instructions further cause the ophthalmic apparatus to perform calculating a positional displacement amount at a preset portion of the subjected eye before and after a surgery by comparing the preoperative two-dimensional tomographic image and the postoperative two-dimensional tomographic image, one of or both of which have been corrected in the correcting of at least one of the two-dimensional tomographic images, the memory is further configured to store information related to the positional displacement amount calculated in the calculating of the positional displacement amount, and the computer-readable instructions further cause the ophthalmic apparatus to perform predicting a shape of the postoperative subjected eye based on the preoperative two-dimensional tomographic image of the preoperative subjected eye acquired by the acquiring of the two-dimensional tomographic image and the information related to the positional displacement amount stored in the memory.

11. The ophthalmic apparatus according to claim 10, wherein the computer-readable instructions further cause the ophthalmic apparatus to perform displaying information related to the preoperative shape of the subjected eye, information related to the postoperative shape of the subjected eye, and the information related to the displacement amount.

12. The ophthalmic apparatus according to claim 11, wherein the information related to the preoperative shape of the subjected eye is the preoperative two-dimensional tomographic image of the preoperative subjected eye, the information related to the postoperative shape of the subjected eye is the postoperative two-dimensional tomographic image of the postoperative subjected eye, the at least one of the preoperative two-dimensional tomographic image of the preoperative subjected eye and the postoperative two-dimensional tomographic image of the postoperative subjected eye is corrected in the correcting of at least one of the two-dimensional tomographic images, and the displaying is configured to display at least one of an image that displays the preoperative two-dimensional tomographic image of the preoperative subjected eye adjacent to the postoperative two-dimensional tomographic image of the postoperative subjected eye, and an image that displays one of the preoperative two-dimensional tomographic image of the preoperative subjected eye and the postoperative two-dimensional tomographic image of the postoperative subjected eye being superimposed over the other thereof.

13. The ophthalmic apparatus according to claim 12, wherein each of the information related to the preoperative shape of the subjected eye and the information related to the postoperative shape of the subjected eye to be displayed by the displaying includes at least one of a corneal shape, shapes of a crystalline lens and an intraocular lens, intraocular positions of the crystalline lens and the intraocular lens, and a shape of an angle of an anterior chamber.

14. The ophthalmic apparatus according to claim 9, wherein the computer-readable instructions further cause the ophthalmic apparatus to perform displaying information related to the preoperative shape of the subjected eye, information related to the postoperative shape of the subjected eye, and the information related to the displacement amount.

15. The ophthalmic apparatus according to claim 14, wherein the information related to the preoperative shape of the subjected eye is the preoperative two-dimensional tomographic image of the preoperative subjected eye, the information related to the postoperative shape of the subjected eye is the postoperative two-dimensional tomographic image of the postoperative subjected eye, the at least one of the preoperative two-dimensional tomographic image of the preoperative subjected eye and the postoperative two-dimensional tomographic image of the postoperative subjected eye is corrected in the correcting of at least one of the two-dimensional tomographic images, and the displaying is performed to display at least one of an image that displays the preoperative two-dimensional tomographic image of the preoperative subjected eye adjacent to the postoperative two-dimensional tomographic image of the postoperative subjected eye, and an image that displays one of the preoperative two-dimensional tomographic image of the preoperative subjected eye and the postoperative two-dimensional tomographic image of the postoperative subjected eye being superimposed over the other thereof.

16. The ophthalmic apparatus according to claim 15, wherein each of the information related to the preoperative shape of the subjected eye and the information related to the postoperative shape of the subjected eye to be displayed by the displaying includes at least one of a corneal shape, shapes of a crystalline lens and an intraocular lens, intraocular positions of the crystalline lens and the intraocular lens, and a shape of an angle of an anterior chamber.

17. The ophthalmic apparatus according to claim 14, wherein each of the information related to the preoperative shape of the subjected eye and the information related to the postoperative shape of the subjected eye to be displayed by the displaying includes at least one of a corneal shape, shapes of a crystalline lens and an intraocular lens, intraocular positions of the crystalline lens and the intraocular lens, and a shape of an angle of an anterior chamber.

18. The ophthalmic apparatus according to claim 1, wherein the computer-readable instructions further cause the ophthalmic apparatus to perform:

acquiring a corneal shape map of the subjected eye; and correcting at least one of a corneal shape map of the preoperative subjected eye and a corneal shape map of the postoperative subjected eye that are acquired by the acquiring of the corneal shape map, based on the calculated displacement amount, to match the first line of reference of the preoperative subjected eye and the second line of reference of the postoperative subjected eye to each other.

19. The ophthalmic apparatus according to claim 18, wherein the computer-readable instructions further cause the ophthalmic apparatus to perform displaying at least one of an image that displays the corneal shape map of the preoperative subjected eye and the corneal shape map of the postoperative subjected eye, one of or both of which have been corrected by the correcting of the at least one of the corneal shape maps, and an image that displays a differential map of the corneal shape map of the preoperative subjected eye and the corneal shape map of the postoperative subjected eye.

\* \* \* \* \*